United States Patent [19]
Goldberger et al.

[11] Patent Number: 4,685,464
[45] Date of Patent: Aug. 11, 1987

[54] DURABLE SENSOR FOR DETECTING OPTICAL PULSES

[75] Inventors: Daniel S. Goldberger, San Fransisco; James E. Corenman, Menlo Park; Kenneth R. McCord, Belmont, all of Calif.

[73] Assignee: Nellcor Incorporated, Hayward, Calif.

[21] Appl. No.: 752,404

[22] Filed: Jul. 5, 1985

[51] Int. Cl.$^4$ .............................................. A61B 5/00
[52] U.S. Cl. ................................. 128/633; 128/664; 128/666; 128/687
[58] Field of Search .................................. 128/632–633, 128/637, 644, 664–667, 672, 677, 686, 327, 346, 687, 689

[56] References Cited

U.S. PATENT DOCUMENTS

| | | | |
|---|---|---|---|
| Re. 30,750 | 9/1981 | Diack et al. | 128/419 D |
| D. 243,038 | 1/1977 | Ray | D83/1 F |
| D. 250,275 | 11/1978 | Bond | D24/29 |
| D. 262,488 | 12/1981 | Rossman et al. | D24/17 |
| 2,358,992 | 9/1944 | Millikan | 356/41 |
| 2,442,462 | 6/1948 | Kirschbaum | 128/633 |
| 2,640,389 | 6/1953 | Liston | 128/633 |
| 2,706,927 | 4/1955 | Wood | 128/633 |
| 2,760,485 | 8/1956 | Adelman | 128/666 |
| 2,790,438 | 4/1957 | Taplin | 128/633 |
| 2,835,252 | 5/1958 | Mauchel | 604/122 |
| 3,152,587 | 10/1964 | Ullrich et al. | 128/633 |
| 3,167,658 | 1/1965 | Richter | 250/239 |
| 3,227,155 | 1/1966 | Erickson et al. | 128/667 |
| 3,229,685 | 1/1966 | Ringkamp et al. | 128/687 |
| 3,359,975 | 12/1967 | Sherman | 128/666 |
| 3,403,555 | 10/1968 | Versaci et al. | 73/861.05 |
| 3,412,729 | 11/1968 | Smith, Jr. | 128/667 X |
| 3,482,565 | 12/1969 | Gowen | 128/667 |
| 3,628,525 | 12/1971 | Polanyi | 128/633 |
| 3,638,640 | 2/1972 | Shaw | 128/633 |
| 3,648,685 | 3/1972 | Hepp et al. | 128/665 |
| 3,704,708 | 12/1972 | Iberall | 128/686 X |
| 3,799,672 | 3/1974 | Vurek | 356/41 |
| 3,810,460 | 5/1974 | Van Nie | 128/666 |
| 3,815,583 | 6/1974 | Scheidt | 128/666 |
| 4,013,067 | 3/1977 | Kresse et al. | 128/666 |
| 4,109,643 | 8/1978 | Bond et al. | 128/666 |
| 4,125,111 | 11/1978 | Hudspeth et al. | 128/689 |
| 4,212,306 | 7/1980 | Mahmud | 128/665 |
| 4,321,930 | 3/1982 | Jobsis et al. | 128/633 |
| 4,334,544 | 6/1982 | Hill et al. | 128/664 |
| 4,380,240 | 4/1983 | Jobsis et al. | 128/633 |
| 4,390,019 | 6/1983 | Leveen et al. | 128/346 X |
| 4,425,921 | 1/1984 | Fujisaki et al. | 128/690 |
| 4,489,725 | 12/1984 | Casey et al. | 128/346 |
| 4,510,938 | 4/1985 | Jobsis et al. | 128/633 |

FOREIGN PATENT DOCUMENTS 2635221 2/1978 Fed. Rep. of Germany ...... 128/666

Primary Examiner—Kyle L. Howell
Assistant Examiner—Angela D. Sykes
Attorney, Agent, or Firm—Robert M. Isackson

[57] ABSTRACT

A sensor for use with instruments that non-invasively measure blood constituents, particularly oxygen saturation of arterial blood from the patient's tissue. The sensor has two rigid housings adapted for arrangement in opposition and secured about a patient's tissue. Each housing has a deformable pad adapted for receiving, conforming to, and securely gripping the patient's tissue without significantly affecting arterial blood flow. In one embodiment, the housings are pivotally mounted and biased closed under tension, one pad contains a light source for illuminating the tissue in its tissue contacting surface, and the other pad contains the light detector for use in measuring the amount of light absorbed by the blood constituent. In a second embodiment one or the other pad contains both the light source and light detector. The detected light can then be correlated to the amount of blood constituent present in the blood.

24 Claims, 13 Drawing Figures

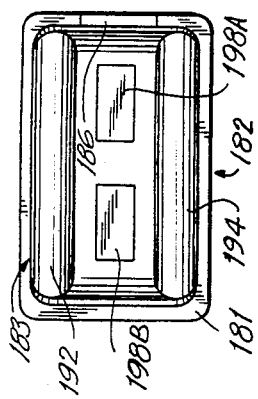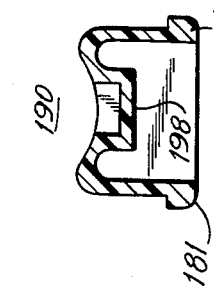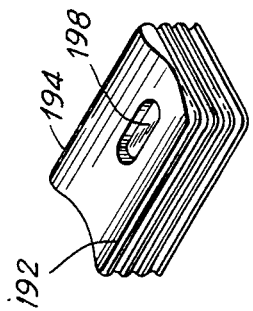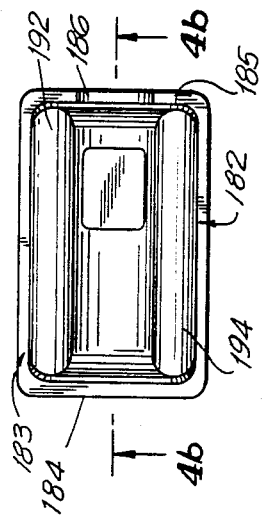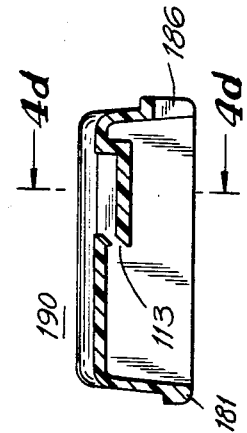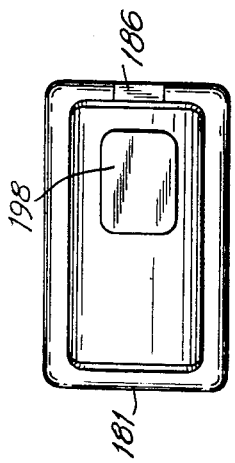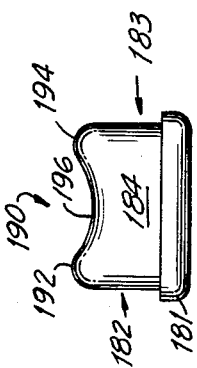

DURABLE SENSOR FOR DETECTING OPTICAL PULSES

This invention relates to a durable sensor for use in detecting arterial blood flow, particularly for use with non-invasive oximetry instruments that measure arterial oxygen saturation and pulse rate.

BACKGROUND OF THE INVENTION

Non-invasive measuring of arterial blood flow characteristics such as arterial pulse rate, oxygen saturation level of hemoglobin in arterial blood, or other blood constituents is common in medical practice The measurements rely on noninvasive sensors that are placed against the patient's tissue at a location where the tissue is well perfused, for example, a fingertip, a toe, the earlobe, the nasal septum, the forehead, the ical cord, and the like. The sensors contain source for passing one or more more wavelengths of light into the perfused tissue and a light detector for detecting the amount of light passing through the tissue. The light source may be an incandescent lamo or one or more light emitting diodes ("LEDs") and the light detector may be a phototransistor, photodiode, or other photodetector. The light detector may be arranged adjacent the light source to detect the amount of light reflected from illuminated tissue such as the forehead or a fingertip, or at a location on the opposite side of the tissue to detect the amount of light passed through the illuminated tissue, such as a fingertip or the bridge of the nose.

The wavelengths used in the sensor are selected for the propensity of the light to be absorbed by the blood constituent being measured. The amount of detected light can then be related to the instantaneous quantity of the blood constituent present in the sample which relationship can be used to determine the amount of the blood constituent in accordance with known procedures, following, for example, Beer's Law. For oxygen saturation measurements, red and infrared wavelengths are typically used. As the oxygen level of the hemoglobin in the blood changes over time, the color of the hemoglobin changes and the amount of red and infrared light absorbed by the hemoglobin changes accordingly. The amount of light detected by the photodetector thus varies in accordance with the varying amount of light absorbed by the tissue and pulsatile arterial blood flow, and, from the amount of light absorbed, oxygen saturation of the blood can be determined. See, for example, the preferred method of calculating blood oxygen saturation (using a non-invasive sensor) described in U.S. patent application Ser. Nos. 718,525, filed April 1, 1985, and 742,720, filed June 7, 1985, both of which are copending and commonly assigned, the disclosure of which are incorporated herein by reference.

The light passing through the tissue is also affected by time invariant factors, including but not limited to skin, skin pigment, bone, nail, hair, other non-moving components, and the like. These factors absorb some of the light illuminating the tissue and the amount of absorption may vary from one patient to another. The intensity of the light from the light source may be adjusted to compensate for such variations and to provide a light bright enough to be detected by the light detector. The detected signal thus contains substantially only the time-varying portion of the light representing the arterial pulsatile flow and the varying amount of blood constituent, for example, oxygenated hemoglobin. The amount of detected light can be correlated to provide the measure of the quantity of the oxygen saturation present in the blood. The technique also can be used for measuring other blood constituents that absorb light of selected frequencies.

Instruments based on this and other similar optical transmission measuring principles have been designed, developed, and are commercially available. Typically, they use two or more wavelengths to measure oxygen saturation and pulse rate. The Nellcor N-100 Oximeter, manufactured by Nellcor Incorporated, Hayward, Calif., is one such instrument. These instruments typically control the transmission of light by the sensor in a pulsed fashion at an appropriate rate, detect the light transmitted, and use sophisticated electronic signal processing devices that process the detected light related information and perform the desired calculations. See U.S. patent application Ser. Nos. 718,525 filed April 1, 1985 and 742,720, filed June 7, 1985.

Known sensors for use with pulse detection (plethysmography) and oxygen detection (oximetry) include reflective mode sensors where the light source and the photodetector are mounted in a rigid surface that is applied to and secured against the tissue by means of a strap about the appendage or the head. See U.S. Pat. Nos. 3,167,658, 4,380,240 and 4,321,930. Alternate forms of reflective mode sensors may include flexible structures that rely on adhesive tape to secure the sensor to the tissue, such as is referred to in U.S. Pat. No. 4,510,938. One reflective mode sensor design provides for a somewhat rigid, but still flexible, conically sectioned sleeve structure that is slipped over a finger until wedged against it, as referred to in U.S. Pat. No. 4,425,921.

Another known form of sensor is a transmissive mode sensor of a clip or clothes-pin type arrangement where one leg has the light source mounted in its rigid flat surface and the opposing leg has the light detector mounted in its rigid flat surface. The two legs are clamped against and on opposite sides of the tissue or an appendage such as a finger or an earlobe. See U.S. Pat. Nos. 3,152,587 and 3,810,460. These clamps may have either a screw arrangement or a spring to secure the sensor legs to the tissue. Other transmissive sensor designs have the light source and light detector mounted in a flexible structure having an adhesive surface for taping the sensor securely around the tissue such as a finger, the foot, or the bridge of the nose. See U.S. patent applications Ser. No. 539,865 filed Oct. 7, 1983 and Ser. No. 493,442 filed May 11, 1983, both of which are copending and commonly assigned. Combined transmissive and reflective sensors designed to selectively detect blood flow from capillary blood flow and palmer finger arteries, as referred to in U.S. Pat. No. 4,013,067, are also known.

One problem with sensors having rigid surfaces containing the light source and light detector is that the surfaces do not conform to the tissue. Rather, the tissue must conform to the sensor in order to provide the close coupling needed to exclude as much ambient light as possible and retain as much light generated by the light source as possible. Close coupling provides for a better signal to noise ratio, a better quality signal and, therefore, more reliable and accurate measurements.

A second problem with rigid housings is that they have a significant mass which can easily become dislodged accidentally, inadvertently, or intentionally, in the course of measuring. Such movement can result in a less than desirable light path, for example, through not well perfused tissue or, in part, not through any tissue. Movement also can change the length or direction of the light path which results in a change in detected light intensity and can affect the calibration of the instrument. These changes can degrade the quality and reliability of the signal and thus the accuracy of the measurements.

To prevent movement, the sensor must be securely held against the tissue by some force. This force consequently exerts pressure on the tissue, which has a tendency to compress the tissue adjacent the sensor, restrict blood flow into the tissue adjacent the sensor, and expel venous blood from the tissue. Such forces can cause reduced arterial or venous blood flow. Further, the hard surfaces may cause localized pressure points which result from the surfaces capturing an area of tissue, pinching it, and thereby causing injury. In addition, rigid sensors can leave compression marks on the tissue which indicates that venous blood has been forced out of the localized area and the blood flow thereto has been altered or minimized. The effect of these results are undesired and not in accordance with generally accepted medical practices for non-invasive measuring techniques and patient well-being. These effects may also operate on normally invariant factors and are work related (pressure, time, distance) so that the quality of the signal may gradually degrade and result in false measurements.

To minimize the impact of the constant pressure exerted by these rigid and massive sensors, the devices must be adjusted or repositioned with regularity. This does not permit long periods of unattended or uninterrupted measurements.

Yet another problem with rigid sensors is that of motion artifact. Motion artifacts are detected pulses that come from muscular or skeletal movement of the tissue or relative movement between the sensor and the tissue. These motions can affect normal pulsatile blood flow causing artificial arterial pulses or change the distance between the light source and the photodetector causing rapid changes in light intensity, each of which can result in erroneous measurements. Motion artifact produces spurious pulses that do not result from true arterial pulsatile flow based upon the heartbeat.

The sensors mounted in flexible structures for contacting the tissue do have conformance to the tissue and, if mounted properly, may not exert any significant pressure against the tissue. However, the pressure is dependent upon the structure's degree of flexibility and how it corresponds to the curvature and flexibility of the tissue. The pressure also depends upon the means for securing the sensor to the tissue, typically a web that is secured about the head or other limb, which is not uniformly controlled or regulated.

Adherent sensors have the advantage that they do not move relative to the tissue, thus reducing the cause of at least one source of measurement error, sensor movement. Adherent flexible sensors have solved some of the problems confronted by the rigid sensors, i.e., conformance, no relative motion, but they have a very short usable lifetime and typically, are restricted to one application. Furthermore, the adhesive surface can lose its adherent quality when moistened for example by blood, body fluids, or perspiration, and does not retain its tackiness beyond a few applications. In addition, adhesives cannot be readily cleaned and sterilized or replaced with any degree of economic efficiency.

It is therefore an object of this invention to provide a durable sensor having a soft deformable pad for contacting and conforming to a variety of different sized tissues for use in connection with detection of selected blood constituents, wherein the sensor may be cleaned and used repeatedly, and will provide accurate, uninterrupted measurements over long periods of time.

Another object of this invention is to provide for a pulse oximeter sensor that is a clothes-pin type clamp for use in detecting oxygen saturation levels from the finger of a patient and exerts enough force to remain secured to the finger even when moved, but not so much force tha& would cause localized pressure points, patient discomfort and compression marks, indicating the blood flow to the region has been altered, or to compress the tissues to such an extent that it affects the accuracy of the measurements over time.

SUMMARY OF THE INVENTION

This invention provides a durable conformable sensor for use with oximetry instruments having a rigid clothes-pin type outer construction comprising two housings pivotally mounted together with the tissue receiving ends urged towards each other. Each housing contains a deformable pad interior to and secured within the housing in the tissue receiving area. The pads are disposed opposite to each other, made of a soft, resilient material, and have a conforming tissue contacting surface configuration that corresponds to and, upon contact with, will conform to a preselected range of tissue sizes to be inserted between the pads. For example, the pads may be disposed about a finger, toe, an infant's hand, ankle, and the like, an umbilical cord, the nasal septum, the bridge of the nose, and the like.

The surface of the pad is designed to be relatively large so that more tissue is contacted and retained by the pad than is required to support the light source against the tissue to perform the measurement. The surface thus distributes the retention force over a large area of the tissue, resulting in a stable attachment both when the finger is stationary and moving. Further, the pad, the housing, or both, also may provide reflective shielding to retain transmitted light in the illuminated tissue, minimize the amount of light passing from the source to the detector that does not pass through the tissue, and reduce the amount of ambient light interfering with transmitted light, and, thus, the measurement.

In one embodiment, the light source, preferably one or more miniaturized LEDs configured on a small integrated circuit, is secured close to the tissue contacting surface of one pad at a location appropriate for passing light through the tissue of a large number of differently proportioned patients. A light detector, preferably a photodiode configured on a small integrated circuit, is secured close to the opposing pad in a position opposite the light source in a transmissive mode, i.e., the light source and light detector are disposed on opposite sides of the tissue through which the light passes. In an alternate embodiment, both the light source and light detector may be secured close to the tissue contacting surface of the same pad as a reflective mode sensor, preferably with an optical barrier separating the source and detector.

In one embodiment, the light source and the light detector are mounted immediately below the surface of the pad in separate depressions and are sealed therein with a clear, resilient material that does not affect appreciably the through transmission of light from the light source to the light detector. In the transmissive mode, the light source and light detector are preferably mounted so that the light passes directly through the tissue from the light source to the light detector for a preselected variety of different sized fingers, for example. In an alternate embodiment, the light source and light detector are affixed to respective spring members and disposed adjacent the pad surface so that when the pad conforms to the tissue, the spring exerts a minimum amount of force sufficient to maintain the light source or detector coupled against the pad when the tissue contacting surface of the pad conforms to the patient's tissue. The amount of force exerted by the spring may be in the range from between about 20 to about 30 grams, for example. Preferably, the actual spring member does not contact the pad.

In the preferred embodiment, the sensor is designed to clamp about a finger of an adult weighing more than about 40 kg. In one embodiment, the deformable pad is comprised of compression molded vulcanized silicone rubber. The tissue contacting surface of the pad is a concave cylindrical section supported by and projecting from a rectangular base, forming a cavity. Two spaced apart longitudinal ridges are molded into the pad at the longitudinal edges of the long side of the cylindrical surface. The ridges provide stability and support to hold onto the finger retained by the pads in the event that the finger moves, voluntarily or involuntarily, and are also useful in orienting the sensor with respect to the finger properly, so that the ridges straddle the top or bottom of the finger. In an alternate embodiment, the deformable pad is comprised of a thin elastic membrane fitted across a frame, for example, latex or silicone rubber. The membrane is relatively taut yet deformable, and the frame is preferably wider than the thickness of the finger or digit against which it will be applied. In this configuration, the membrane preferably is clear so that it does not appreciably affect the through transmission of light and the light source and detectors are mounted on the spring members adjacent and interior to their respective membranes.

The actual configuration of the tissue contacting pad is a result of balancing the need to conform the pad to the finger, and thereby closely couple the light source and light detector to the tissue, and the pressure requirement to hold the pad onto the finger or digit without undue force. The design also must strike a compromise to enable the sensor to be used with a range of finger sizes.

In the preferred embodiment, the amount of force exerted on the finger is in the range between from about 150 to about 250 grams, as measured by the force required to open the extensions. The retention force may be provided by a spring such as a double torsion spring fitted about the pivot connecting the housings. The magnitude of the force is large enough to keep the sensor on the finger but is not so great as to expel venous blood from the contact area, affect the arterial or venous blood flow, cause localized pressure points, patient discomfort or compression marks, or affect the calibration of the instrument.

One advantage of this invention is that it provides a durable sensor having a tissue contacting surface that conforms to the tissue, rather than the tissue having to conform to a rigid surface, and the amount of pressure needed to maintain the deformable sensor in position does not significantly affect blood flow detrimentally, or injure or discomfort the patient.

A further advantage of this invention is that it provides a durable sensor that is easy to use and operates comparable to an adhesive type sensor yet may be readily cleaned by conventional medical sterilants and has a long useable lifetime.

Another advantage of this invention is that the sensor can be attached to a patient for long periods of time without having to frequently readjust the position of the sensor.

Yet another advantage of this invention is that the materials used are long lasting, and their color is controlled to reduce the interference caused by ambient light without significantly absorbing the wavelength of interest, providing a readily detectable signal for use in performing the measurement calculations.

BRIEF DESCRIPTION OF THE DRAWINGS

FIG. 3 is a cross sectional view taken along lines A—A of FIG. 1.

FIG. 4a is a top view of the deformable pad of FIG. 2.

FIG. 4b is a cross sectional view taken along lines 4b—4b of FIG. 4a.

FIG. 4c is a front end view of the pad of FIG. 4a.

FIG. 4d is a cross sectional view taken along lines 4d-4d of FIG. 4b.

FIG. 4e is a bottom view of FIG. 1.

FIG. 4f is a top view of a deformable pad in accordance with an alternate embodiment of this invention.

FIG. 4g is a perspective view of a deformable pad in accordance with an alternate embodiment of this invention.

FIG. 5b is a cross-sectional view taken along lines 5b—5b of FIG. 5a.

FIG. 5c is a top view of FIG. 5a.

DETAILED DESCRIPTION OF THE INVENTION

Figure 1:
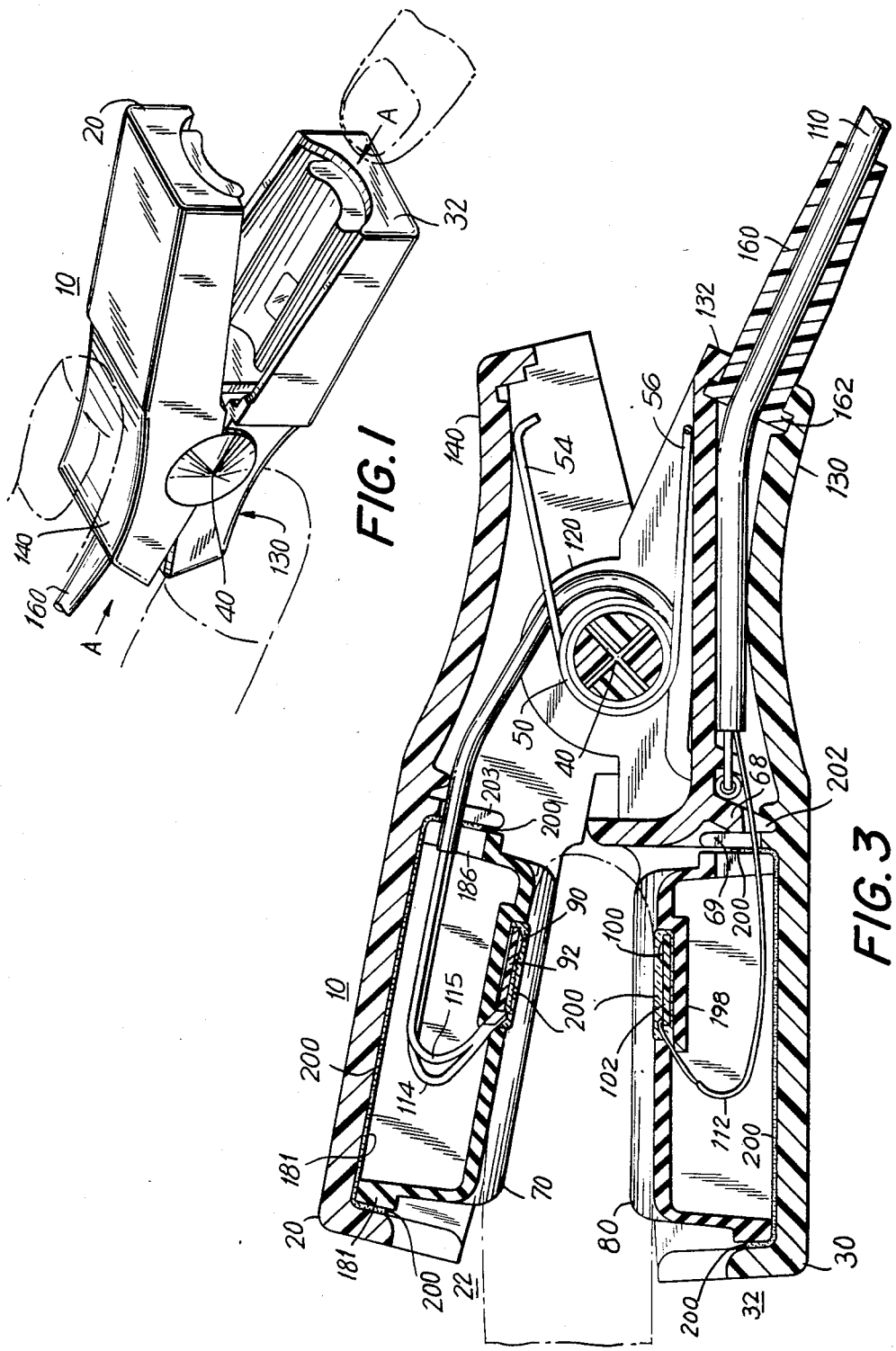
FIG. 1 is a front perspective view of a sensor in accordance with this invention.

As shown in the FIGS. 1—4, one embodiment of this invention comprises a sensor 10 comprising first housing 20, second housing 30, pivot 40, spring 50, finger stop 60, first deformable pad 70, second deformable pad 80, light source 90, light detector 100 and signal cable 110.

Housings 20 and 30 are substantially identical in form and function. Each has a rectangular-like extension for receiving their respective deformable pads, a pair of bosses 120 having apertures for receiving pivot 40, and pinch sections 140 and 130 to be pushed towards each other to separate ends 22 and 32 of the rectangular extensions of housing 20 and 30 so that a finger or digit may inserted. Spring 50 is preferably a double torsion spring that provides the force to bias housing extension ends 22 and 32 closed, with or without a finger therebetween. A double torsion spring is preferred because such springs exert a nearly constant force while operating within the prescribed operating range which is advantageous in maintaining the 150-250 gram force on the finger, for the selected range of finger thicknesses. Other spring means could be used to accomplish the same result.

Spring 50 is arranged so that pivot 40 will pass through coiled central portions 52, both long spring members 54 are urged against the inside of curved section 140 of housing 20, and long spring member 56 is urged against finger stop 60. Housings 20 and 30 are formed with stops (not shown) to prevent compressing deformable pads 70 and 80 when nothing is between the pads. Ends 22 and 32 each have a curved shape so that when a finger is inserted between pads 70 and 80, the finger does not contact the rigid material of housings 20 and 30.

Housings 20 and 30 are arranged opposite each other so that the tissue contacting surface of pads 70 and 80 face each other and bosses 120 align permitting pivot 40 to be inserted therethrough. Pivot 40 comprises two conventional split-legged pieces that snap together and interlock to form a cylindrical pivot. See FIG. 2.

The force exerted by spring 50 is preferably in the range from about 150 grams to about 250 grams as measured by the force required to open housing extension ends 22 and 32. This force, in conjunction with the resiliency of deformable pads 70 and 80, is sufficient to retain sensor 10 on the patient's finger to obtain good optical coupling, to prevent the sensor from falling off during movement (except with some effort) and while at the same time not exerting such pressure on the tissue that would cause localized pressure points, patient discomfort, and compression marks, create erroneous measurements, or otherwise adversely affect or alter the blood flow. In the event that measurements are to be taken on another area of the patient such as the nasal septum, the umbilical cord, the finger, the hand or ankle of an infant, or the like, then the spring force required, as well as the tissue receiving structures, may have to be modified as appropriate.

Figure 2:
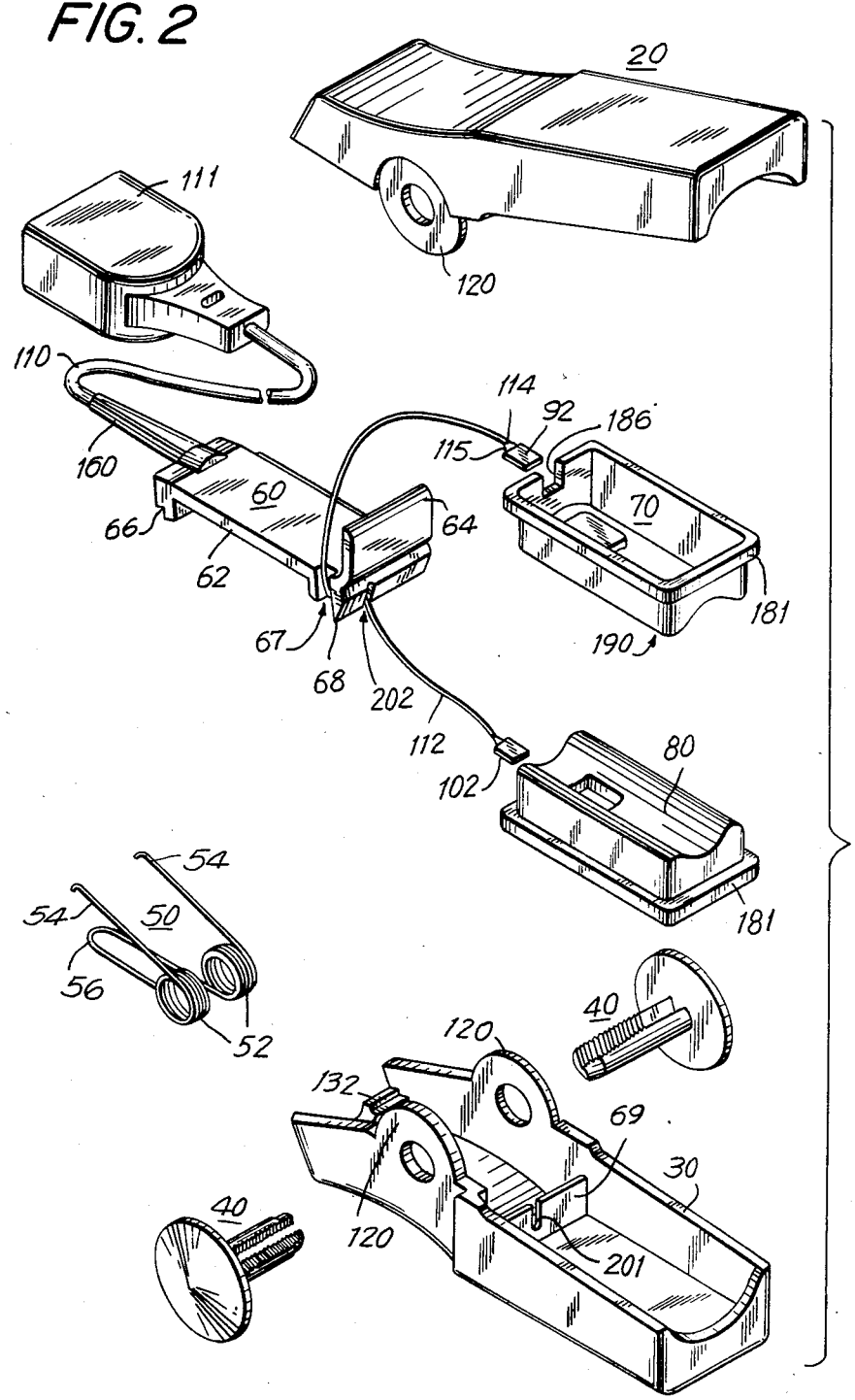
FIG. 2 is an exploded perspective view of the sensor of FIG. 1.

Referring to FIGS. 2 and 3, housing 30 is referred to as the bottom piece. It has secured to it at curved section 130 finger stop 60. Finger stop 60 is an L-shaped member having long section 62, short section 64, lip 66, and retention protusion 68. The height of short leg 64 is designed to permit a finger nail, especially a long fingernail, to pass over the top but to prevent the fleshy fingertip from entering the opened housing extensions beyond a selected point. Short leg 64 thus provides for placing the patient's finger at an appropriate location relative to the light source and the light detector for optical transmission therethrough, the location preferably being near the cuticle for the majority of the finger sizes for which the particularly dimensioned sensor is applicable. Stop 60 is secured into housing 30 preferably by means of an adhesive such as Superbonder #414, available from Loctite Corporation, Newington, Conn., applied between the tip of retention protusion 68 and the housing.

Between finger stop 60 and the inside of extension 30 is signal cable 110. Cable 110 is passed through flexible strain relief member 160, preferably made from a general purpose polyvinyl chloride material having a 50-60 Shore-A durometer hardness, which has flanged section 162 that can be secured between lip 66 of stop 60 and back end 132 of housing 30. Cable 110 may be secured to stop 60 by an adhesive such as Superbonder #414 a snap-in S-shaped cable receptacle (not shown), or both. In an alternative embodiment, finger stop 60 and cable 110 may be assembled in housing 20 instead of housing 30.

At one end of cable 110 is connector 111 designed to connect the wiring to the blood constituent measuring instrument being used. Cable 110 comprises four wires, two of which are wrapped in subcable 112 and are electrically connected to photodetector 100 on integrated circuit 102, and wires 114 and 115 which are electrically connected to light source 90 on integrated circuit 92. Light source 90 preferably comprises a red LED and an infrared LED that are strobed sequentially under the control of the blood constituent measuring instrument in accordance with procedures known to those skilled in the art. The red LED preferably operates at a wavelength of about 660 nanometers and the infrared LED operates at about 920 nanometers, nominally.

Referring to FIG. 2 and FIGS. 4a-4e, deformable pads 70 and 80 are substantially identical in structure. For convenience, the discussion will refer to only one pad unless otherwise stated, although the discussion applies to both pads. The pads are formed and vulcanized by compression molding silicone rubber, optionally of medical grade, into the tissue receiving configuration having about a 10 Shore-A durometer hardness. The desired characteristics that make compression molded silicone rubber particularly suited for use as a deformable pad include, but are not limited to, its resiliency, flexibility, durability, and resistance to solvents, the ability to clean silicone in accordance with common medical practices, and a relatively high coefficient of friction relative to skin, i.e., about 0.95, so that it will not easily slide off a clamped finger. Similar materials exhibiting some or all of these traits may also be used.

In a preferred embodiment, the pad configuration includes rectangular base 181 which can be adhered to the respective insides of the rectangular extension areas of housing 20 and 30, in opposition, preferably by means of a sealant such as Silastic 3140 RTV manufactured by Dow Corning Corporation, Midland, Mich., or an equivalent (see FIG. 3 where sealant 200 is shown). Extending upwardly and offset inwardly from base 181 are four walls 182–185 roughly perpendicular to the plane of the rectangular base. Longer dimensioned walls 182 and 183 are parallel to one another and terminate at the tissue contacting surface. Shorter dimensioned walls 184 and 185 are also parallel to one another and terminate in the cylindrical form of concave surface 196. Wall 185 has aperture 186 for receiving a wire for either light source 90 or light detector 100 into the interior of the pad.

Tissue contacting surface 190 comprises spaced apart parallel ridges 192 and 194 terminating in walls 182 and 183, and concave cylindrical section 196 interconnecting ridges 192 and 194. Section 196 smoothly interfaces with all four walls 182–185 to form arcuate surfaces at a preselected radius of about 0.093 inches and has depression 198 in a location generally equidistant from ridges 192 and 194 and about ⅓ of the length along the ridges from wall 183 for receiving one of light source 90 or light detector 100.

Slit 113 (see FIG. 4b) is provided in depression 198 so that small integrated circuit 102 or 92 can be inserted into depression 198 from inside the cavity formed by walls 182–185 and tissue contacting surface 190. Thus, light source 90 or light detector 100 can be placed inside the depression and arranged so that the light emitting side or light detecting side faces the opposing pad. The depression with the integrated circuit therein is then filled with a sealant material that will not interfere appreciably with the optical transmission from light source 90 to detector 100, preferably will remain flexible, and will provide a surface which may or may not be curved in conformance with cylindrical tissue contacting surface 196. The preferred sealant is a room temperature vulcanizing (RTV) encapsulating material such as Silastic 3140 RTV or an equivalent.

Pads 70 and 80 are preferably compression molded to the desired shape having a relatively uniform thickness in the range from about 0.030" to about 0.050" to provide sufficient support so that the pads will conform to a finger, will not collapse when closed about a finger, and yet are not so rigid as to affect the flow of blood into the areas, cause pressure points, patient discomfort, or compression marks, or affect the accuracy of the measurements by significantly deforming the tissue. The resiliency of the pad absorbs some of the force generated by spring 50 and spreads the force along the interface between pads 70 and 80 and the tissue. Ridges 192 and 194 aid in distributing the force along tissue contacting surface 190, which has enough resiliency to conform to the tissue with which it is in contact, and thereby prevent any localized pressure spots that could adversely affect the tissue or blood flow measurements being taken. Ridges 192 and 194 also help orient sensor 10 relative to the finger so that the deformable pads can straddle and be closed about the finger and maintain the hold of sensor 10 for a variety of different sized fingers for which preferred sensor 10 can be used.

The color of the pad may be selected for its light absorption and reflectance qualities. In the preferred embodiment, the color is selected to reflect all light of the wavelengths generated by light source 90, so as to maximize the intensity of the optical transmission and the amount of light diffused in and attenuated by the tissue. If the pad were to absorb too much light, light source 90 would have to be of greater intensity which, for example, could affect the longevity of the sensor or distort the measurements because of an unfavorable signal to noise ratio. Ideally, pads 70 and 80 should reflect the wavelength of interest and absorb all other wavelengths so as to permit maximizing the signal to noise ratio and provide more accurate measurements. Because it is difficult to find a frequency selective reflector that will absorb other wavelengths, some experimentation may be necessary to find an appropriate color to use. In the preferred embodiment, a pearl white color was selected as the best compromise. Other colors such as black, blue, or tan yielded functional, but less desirable, results.

The configuration of tissue contacting surface 196 also can be constructed to reflect the transmitted light towards the light detector and otherwise keep the tissue illuminated so that the light can be absorbed by the blood constituent being measured, e.g., oxygen saturation of the hemoglobin. This aids in maintaining a sufficient signal to noise ratio. The color of the pads can also affect how much ambient or environmental light can be prevented from interferring with light detector 100. Thus, a high signal to noise ratio can be maintained by reflecting the transmitted light from light source 90 back into the tissue, absorbing all other light interior to tissue contacting surfaces 190 of opposing pads 70 and 80, and reducing the interference caused by ambient light either by reflection or absorption of the same.

Referring to FIGS. 2 and 3, it can be seen that wires 112 are threaded through aperture 202 of retention protusion 68 and aperture 201 in protusion 69, through aperture 186 of pad 80 into the interior cavity of pad 80, and through slit 113 in depression 198 where it is sealed therein by sealing material 200. The sub-cable containing wires 114 and 115 is threaded through side aperture 67 in finger stop 60 behind pivot 40 and center coil sections 52 of spring 50 through aperture 203 of extension 20, through aperture 186 of pad 70 into the interior cavity of pad 70, through slit 113 in depression 198 of pad 70 where it is secured by sealing material 200. Light source LEDs 90 and light detector photodiode 100 are preferably disposed equidistant from the center of pivot 40 and along the centerline of their respective rectangular extensions of housings 20 and 30.

Pads 70 and 80 are not air tight and do not rely on air pressure to resist collapse due to applied pressure. While air pressure resistance could be used in addition to structural rigidity to control deformation, the occurrence of pin holes, cracks or other leaks could substantially reduce the effectiveness and lifetime of such a sensor. Relying only on structural rigidity for controlled deformation avoids the risks associated with sealed pads. Furthermore, by permitting the interior cavity of pads 70 and 80 to have air exchange, the sterilants used to clean the sensor can penetrate the cavity, thereby significantly reducing the risk of infection resulting from use of the sensor. Cleanliness is especially important because an intended use of the sensor is in connection with monitoring anesthetized patients during surgery.

Extensions 20 and 30 are comprised of a rigid material, preferably injection molded rigid thermoplastic material such as Mobay Merlon FCR 2405 polycarbonate. The color of housings 20 and 30 may be selected for desired light reflection and absorption properties as discussed above in connection with the color of deformable pads 70 and 80. Further, the material, color, and configuration of the housing may be selected to minimize the optical crosstalk, that is, to prevent the light generated by light source 90 and ambient light from passing to detector 100 without first having been diffused and attenuated by being passed through the tissue This attenuation aids in maintaining a quality signal for obtaining accurate measurements In the preferred embodiment, the color chosen was pearl 2440 in accordance with Borg Warner A.B.S. "Spectrum" color standards or an equivalent, primarily because that color reflects most ambient light well. In an alternate embodiment housings 20 and 30 could have a highly reflective color on the exterior to reflect ambient light, and a highly absorbent color on the interior to absorb what ambient light penetrates the interior of the housings which may or may not be reflected off pads 70 or 80.

Referring to FIG. 4f, an alternate embodiment of deformable pad 70a in accordance with this invention is shown. In this embodiment, pad 70 a contains two depressions 198a and 198b for receiving light source 90 and light detector 100, respectively, or vice versa. Each depression is about equidistant from ridges 192 and 194 and has a slit (not shown) through which light source 90 or light detector 100 may be inserted before depressions 198a and 198b are filled with sealant material 200. Because having two depressions in the same pad is likely to change the deformability of the pad, some modification of ridges 192 and 194 or concave surface 196 may be necessary for proper conformance. In this reflective mode embodiment, the tissue contacting surface of the opposing pad (not illustrated) may be identical to pad 70a and, preferably, would be deformable, have a silicone rubber surface, and have a substantially smooth concave surface.

In yet another embodiment, more than one light sensor or detector could be placed in either or both of the pads to provide, for example, redundant measurements or measurements of more than one blood constituent with the same sensor.

Figure 5A:
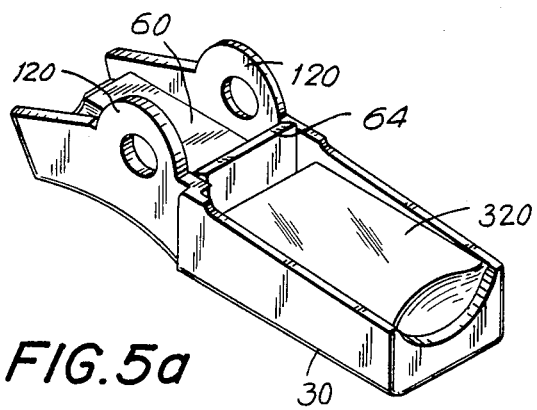
FIG. 5a is a perspective view of a deformable pad in accordance with an alternate embodiment of this invention.
Figure 5B:
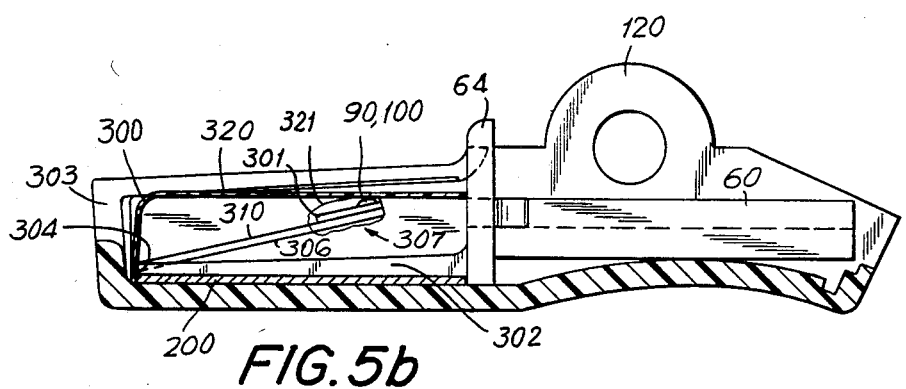
Figure 5C:
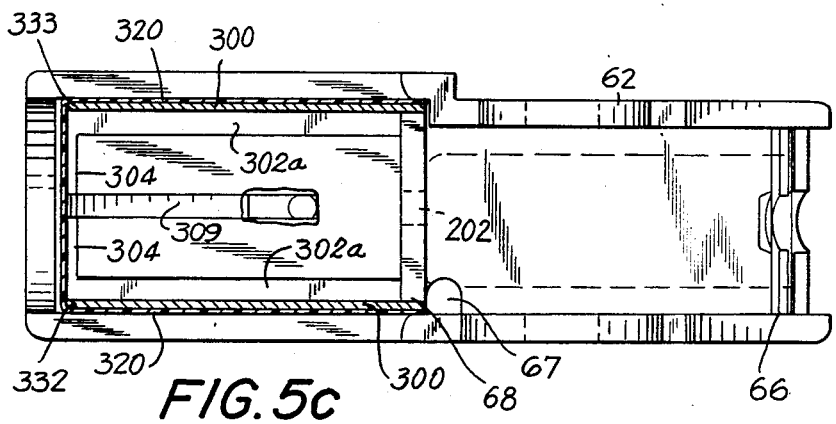

Referring to FIGS. 5a-5c, an alternate embodiment of pad 80 is shown. (The same reference numbers as used in FIGS. 1-4 are used where applicable and, although only one pad is discussed, the discussion applies to the opposing pad as well.) Interior to the extension of housing 30 is frame 300, spring 310, and thin membrane 320. Spring 310 comprises finger stop 60, preferably as shown in FIG. 2, including long leg 62, lip 66, side aperture 67, protusion 68, and aperture 202. At the front of protusion 68 extend two substantially parallel members 302a and 302b and cross member 304 joining members 302a and 302b together. At the midpoint of cross member 304 extends holder member 306. Secured at end 307 of holder member 306 is one of either light source 90 or light detector 100 (or their respective integrated circuits 92 and 102). Holder member 306 rises from the plane formed by members 302a and 302b at an angle sufficient to place light source 90 or light detector 100 in close proximity to thin membrane 320.

Holder member 306 is joined to cross member 304 so that first, when there is no load on thin membrane 320, light source 90 or detector 100 is just above, at, or immediately below the surface of thin membrane 320, and second, when there is a load on thin membrane 320, causing it to conform to the load, the force exerted by spring 310 or membrane 320 is sufficient to maintain holder member 306 sufficiently rigid to keep source 90 or detector 100 abutted against membrane 320 and closely couple to the tissue optically, while not causing a localized pressure point, patient discomfort or compression marks, or otherwise appreciably affecting the flow of blood near the point of contact adversely. In accordance with this embodiment, the amount of force exerted by spring 310 against membrane 320 is in the range between from about 20 grams to about 30 grams.

Light source 90 or light detector 100, or their respective integrated circuits, are attached to holder member 306, preferably at end 307, by any conventional means, including but not limited to the application.of a thermosetting adhesive, or by shrinking a tube of heat shrink material 321 (FIG. 5b) about the assembly. The heat shrink material may be conventional and should be selected so that it does not affect appreciably the through transmission of light. The strength of spring members 302, 304, 306 are dependent upon the dimensions of the sensor, the size of the tissue contacting surface area, the expected range of travel of member 306, and the weight of integrated circuit 301 containing light source 90 or light detector 100 and its related wires. Thus, the actual configuration may require some selection of parameters, particularly a resilient spring member with a significant range of motion but only a minimal resistive force in the aforementioned range.

Frame 300 may comprise two or more parallel plates 332 and 333 having smooth or rounded edges so as not to tear thin membrane 320, and may be retained between housing 30 and member 302a and between housing 30 and member 302b, respectively. Frame 300 may be relatively rigid to support membrane 320, and may be stainless steel, for example.

Thin membrane 320 is formed as a film and applied over frame 300, preferably completely enclosing spring 310 so as not to risk tearing an exposed edge of the film during use. Frame 300 may be secured within housing 30, before or after membrane 30 is applied thereto, preferably after, by any conventional means. In one embodiment, frame 300 may be fitted about members 302 and 304 and restrained in its proper location by securing spring 310 (including finger stop 60) into housing 30.

Thin membrane 320 is preferably a thin elastic material, in the range from between about 10 to about 15 thousandths of an inch thick. Such materials include, but are not limited to a conventional latex material such as that manufactured by Hyginic, Akron, Ohio, or a silicone rubber material Membrane 320 must be resilient, flexible and durable, deformable, have a high coefficient of friction with respect to tissue, and be cleanable in accordance with common medical practice. Membrane 320 is preferably clear so that it does not appreciably affect the through transmission of light, but it may be colored, in part or in whole, by application of pigment or a colored coating so as to provide the desired light absorption and reflection characteristics mentioned in connection with the compression molded silicone pads. If membrane 320 is clear, then the color of spring 310, frame 300, and interior of housing 30 may be selected to provide the desired light absorption and reflection qualities.

Other forms of deformable pads and other processes of forming the pads could be used rather than the preferred compression molded silicone rubber and thin elastic membrane pads. For example, open or closed cell foam having tissue contacting surfaces could be sculptured to accommodate the tissues to be measured. Similarly a deformable gel within a retaining membrane could be used. One other such configuration may utilize beveled side walls for each of walls 182-185 as shown in FIG. 4g.

We claim:

1. A sensor for use in illuminating a patient's tissue to measure blood constituents, comprising:

a first housing;

a first deformable means for securely gripping and complying to the patient's tissue, attached to the first housing and having an undeformed shape when not complying to the tissue;

a second housing;

a second deformable means for securely gripping and complying to the patient's tissue, attached to the second housing and having an undeformed shape when not complying to the tissue;

a light source secured proximal to the surface of one of the first or second deformable means;

a light detector secured proximal to the surface of the other of the first or second deformable means;

means for arranging the first and second housings so that the first and second deformable means are in opposition about the patient's tissue; and means for connecting the first and second housings together about the patient's tissue so that the first and second deformable means grip and conform to the shape of the tissue without substantially altering the blood flow and for disengaging the sensor from the tissue to permit the first and second deformable means to return to their undeformed shape.

2. The sensor of claim 1 wherein the first deformable means further comprises a deformable pad having a tissue contacting surface adapted for gripping and complying to the patient's tissue, and the second deformable means further comprises a deformable pad having a tissue contacting surface adapted for gripping and complying to the patient's tissue.

3. A sensor for use in illuminating a patient's tissue to measure blood contituents, comprising:
two rigid housings pivotally connected, the housings having an open position and a closed position with respect to one another;
means for biasing the housings in their closed position;
a pair of deformable means for securely gripping and complying to the pateint's tissue, each having an undeformed shape when not complying to the tissue, secured on opposing surfaces of the housings between the pivotal connection and the housing ends;
a light source secured proximal to the surface of the deformable means on one said housing;
a light detector secured proximal to the surface of the deformable means on the other said housing; and
means for opening and closing the housings to permit the patient's tissue to be inserted into the sensor and the deformable means to grip and conform to the shape of the tissue without substantially altering the blood flow and to permit the patient's tissue to be removed from the sensor and the deformable means to return to their undeformed shape.

4. The sensor of claim 3 further comprising:
means for locating the patient's tissue relative to the light source and light detector so that the light travelling from the source to the detector transilluminates and is at least partially absorbed by the tissue.

5. The sensor of claim 3 wherein the patient's tissue is a digit and wherein each deformable pad further comprises:
a tissue contacting surface having a concave section extending along the length of the pad and a pair of ridges on which the digit may rest extending along the edges of the concave section;
each tissue contacting surface being adapted for receiving and conforming to the top or the bottom of the digit,
the light source and the light detector each being positioned substantially equidistantly between the ridges of its respective pad; and
the sensor being adapted for orientation relative to the digit so that the light source and the light detector are closely coupled to one or the other of the top or bottom of the digit and the opposing ridges and cylindrical sections of said pads securely grip and conform to the digit.

6. The sensor of claim 5 further comprising:
a depression in the tissue contacting surface of each said deformable pad;
an aperture in each said depression through which one of a light source or light detector may be passed; and
means for sealing the light source or light detector in the depression, said sealing means not appreciably interfering with the optical transmission of light from the light source through said sealing means.

7. The sensor of claim 6 wherein the deformable pad further comprises a cavity formed between the tissue contacting surface and the housing to which the pad is attached, said cavity being in open communication with the atmosphere and having a first volume when the patient's tissue is inserted into the sensor and a second volume when no tissue is inserted into the sensor.

8. The sensor of claim 3 wherein the patient's tissue is a digit and wherein each deformable pad further comprises:
a frame mounted on the housing;
a membrane mounted on the frame, the membrane being a thin resilient layer and having a tissue contacting surface; and
a spring member receiving one of the light source or light detector and arranged between the housing and the membrane so that the source or detector is disposed adjacent the membrane and adapted for optical coupling to the patient's digit when the digit is inserted into the sensor.

9. The sensor of claim 3 wherein the light source comprises light emitting diodes.

10. The sensor of claim 3 wherein the deformable pads further comprise silicone rubber.

11. The sensor of claim 3 wherein the biasing means is a double torsion spring.

12. The sensor of claim 3 wherein each deformable means further comprises a deformable pad having a tissue contacting surface adapted for gripping and complying to the patient's tissue.

13. A sensor for use in illuminating a patient's tissue to measure blood constituents comprising:
a first housing;
a first deformable means for securely gripping and complying to the patient's tissue, attached to the first housing and having an undeformed shape when not complying to the tissue;
a second housing;
a second deformable means for securely gripping and complying to the patient's tissue, attached to the second housing and having an undeformed shape when not complying to the tissue;
a light source secured proximal to the surface of the one of the first or second deformable means on one said housing;
a light detector secured proximal to the surface of the same deformable means on the same said housing;
means for arranging the first and second housings so that the first and second deformable means are in opposition about the patient's tissue; and
means for connecting the first and second housings together about the patient's tissue without substantially altering the blood flow so that the first and second deformable means grip and conform to the shape of the tissue and for disengaging the sensor from the tissue to permit the first and second deformable means to return to their undeformed shapes.

14. The sensor of claim 13 wherein the first deformable means further comprises a deformable pad having a tissue contacting surface adapted for gripping and complying to the patient's tissue, and the second deformable means further comprises a deformable pad having a tissue contacting surface adapted for gripping and complying to the patient's tissue.

15. A sensor for use in illuminating a patient's tissue to measure blood constituents, comprising:
two rigid housings pivotally connected, the housings having an open position and a closed position;
means for biasing the housings in their closed position;
a pair of deformable means for securely gripping and complying to the patient's tissue, each having an undeformed shape when not complying to the tissie, secured on opposing surfaces of the housing between the pivotal connection and the housing ends;

a light source secured proximal to the surface of the deformable means on one said housing;

a light detector secured proximal to the surface of the deformable means on the same said housing; and means for opening and closing the housings to permit the patient's tissue to be inserted into the sensor and the deformable means to conform to the shape of the tissue without substantially altering the blood flow and to permit the patient's tissue to be removed from the sensor and the deformable means to return to their undeformed shape.

16. The sensor of claim 15, further comprising:
means for locating the patient's tissue relative to the light source and light detector so that the light from the source illuminates and is at least partially absorbed by the tissue, and is detected by the light detector.

17. The sensor of claim 15, wherein the patient's tissue is a digit and wherein each deformable pad further comprises:
a tissue contacting surface having a concave section extending along the length of the pad and a pair of ridges on which a digit may rest extending along the edges of the concave section;
each tissue contacting surface being adapted for receiving and conforming to the top or the bottom of the digit;
the light source and the light detector being each positioned substantially equidistantly between the ridges of the same pad; and
the sensor being adapted for orientation relative to the digit so that the light source and the light detector are closely coupled to one of the top or bottom of the digit and the opposing ridges and cylindrical sections of said pads securely grip and conform to the digit.

18. The sensor of claim 17, further comprising:
a depression in the tissue contacting surface of one or the other of said deformable pads;
an aperture in said depression through which the light source and light detector may be passed; and
means for sealing the light source and light detector in the depression, said sealing means not appreciably interfering with the optical transmission of light from the light source through said sealing means.

19. The sensor of claim 18 wherein the deformable pad further comprises a cavity formed between the tissue contacting surface and the housing to which the pad is attached, said cavity being in open communication with the atmosphere and having a first volume when the patient's tissue is inserted into the sensor and a second volume when no tissue is inserted into the sensor.

20. The sensor of claim 15 wherein the patient's tissue is a digit and wherein at least one of the deformable pads further comprises:
a frame mounted on the housing;
a membrane mounted on the frame, the membrane being a thin resilient layer and having a tissue contacting surface;
a spring member receiving one of the light source or light detector and arranged between the housing and the membrane so that the source or detector is disposed adjacent the membrane and adapted for optical coupling to the patient's digit when the digit is inserted into the sensor; and
a spring member receiving the other of the light source or light detector and arranged between the housing and the membrane so that the source or detector is disposed adjacent the membrane and adapted for optical coupling to the patient's digit when the digit is inserted into the sensor.

21. The sensor of claim 15 wherein the light source comprises light emitting diodes.

22. The sensor of claim 15 wherein the deformable pads further comprise silicone rubber.

23. The sensor of claim 15 wherein the biasing means is a double torsion spring.

24. The sensor of claim 15 wherein each deformable means further comprises a deformable pad having a tissue contacting surface adapted for gripping and complying to the patient's tissue.

* * * * *

UNITED STATES PATENT AND TRADEMARK OFFICE
CERTIFICATE OF CORRECTION

PATENT NO. : 4,685,464

DATED : August 11, 1987

INVENTOR(S) : Goldberger et al.

It is certified that error appears in the above-identified patent and that said Letters Patent is hereby corrected as shown below:

```
Column 1, line 14, after "practice" insert --.--;
column 1, line 19, after "contain", insert --a light--;
column 1, line 23, "lamo" should be --lamp--;
column 1, line 62, "adjusted" should be --adjusted--;
column 3, line 36, after "artifact" insert --.--;
column 4, line 13, "tha&" should be --that--;
column 6, line 59, "may" should be --may be--;
column 10, line 39, after "tissue" insert --.--;
column 10, line 41, after "measurements" insert --.--; and
column 14, lines 67-68, "tissie" should be --tissue--.
```

Signed and Sealed this

Twenty-second Day of March, 1988

Attest:

DONALD J. QUIGG

*Attesting Officer*  *Commissioner of Patents and Trademarks*